United States Patent [19]

Grayson

[11] Patent Number: 4,723,017

[45] Date of Patent: Feb. 2, 1988

[54] PROCESS FOR PREPARING 3-HYDROXY-3-(2-METHYL-5-PYRIDYL)-PROPIONIC ACID ALKYL ESTERS

[75] Inventor: James I. Grayson, Durham, England

[73] Assignee: Lonza Ltd., Gampel/Valais, Switzerland

[21] Appl. No.: 946,077

[22] Filed: Dec. 24, 1986

Related U.S. Application Data

[62] Division of Ser. No. 870,390, Jun. 4, 1986, Pat. No. 4,687,856.

[30] Foreign Application Priority Data

Jun. 20, 1985 [CH] Switzerland ............... 2614/85

[51] Int. Cl.$^4$ ............................................. C07D 213/30
[52] U.S. Cl. ................................................. 546/341
[58] Field of Search ......................................... 546/341

[56] References Cited

U.S. PATENT DOCUMENTS 4,579,953  4/1986  Grayson .................. 546/318

FOREIGN PATENT DOCUMENTS 0003677  2/1979  European Pat. Off. ......... 546/318
 654577  2/1986  Switzerland ................ 546/318

OTHER PUBLICATIONS

Drugs of the Future, 7, 157 (1982).
Graef et al., J. Org. Chem., 11, 257 (1946).

Primary Examiner—Henry R. Jiles
Assistant Examiner—J. Richter
Attorney, Agent, or Firm—Fisher, Christen & Sabol

[57] ABSTRACT

3-Hydroxy-3-(2-methyl-5-pyridyl)-propionic acid alkyl esters which, as intermediate products that can be industrially produced in a simple manner, can be used for the production of 2-methylpyridine-5-propionic acid alkyl ester.

21 Claims, No Drawings

PROCESS FOR PREPARING 3-HYDROXY-3-(2-METHYL-5-PYRIDYL)-PROPIONIC ACID ALKYL ESTERS

This is a divisional of application Ser. No. 870,390, filed on June 4, 1986, now U.S. Pat. No. 4,687,856.

BACKGROUND OF THE INVENTION

1. Field of the Invention

The invention relates to new 3-hydroxy-3-(2-methyl-5-pyridyl)-propionic acid alkyl esters, a process for the production of such compounds and the use of such compounds for the production of 2-methylpyridine-5-propionic acid alkyl esters.

2. Prior Art

2-Methylpyridine-5-propionic acid alkyl esters are important intermediate products for a series of new histamine $H_1$ and $H_2$ antagonists [Drugs of the Future, 7, 157 (1982)].

3-Pyridine propionic acid ethyl esters have been produced in a yield of 92 percent by the hydrogenation of nicotinoyl acetate in the presence of a palladium/-barium sulfate catalyst [Graef et al., J. Org. Chem., 11, 257, (1946)]. As the tests of the applicant herein prove, the reaction cannot be transferred to 6-methyl nicotinoyl acetate. Further, it is known to produce 2-methylpyridine-5-alkyl propionic acid alkyl ester starting from 6-methylpyridine-3-carbaldehyde by a three-stage synthesis (European Patent Application 0003677). But in such process, it is disadvantageous that the starting product, 6-methylpyridine-3-carbaldehyde, must be produced from 2-methyl-5-vinylpyridine that is difficult to obtain and is very expensive.

BROAD DESCRIPTION OF THE INVENTION

The main object of the invention is to provide a simpler, industrially- and economically-feasible way to produce 2-methylpyridine-5-alkyl propionates.

The main object of the invention is attained by the use of new 3-hydroxy-3-(2-methyl-5-pyridyl)-propionic acid alkyl esters of the formula:

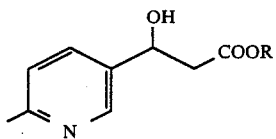

wherein R is a lower alkyl group. Advantageously, the lower alkyl group is an alkyl group having 1 to 4 carbon atoms which can be straight-chain or branched, but R is preferably a methyl or ethyl group.

Production of the new invention compounds is achieved by starting from 5-ethyl-2-methyl pyridine, which is converted to a 6-methyl alkyl nicotinate by oxidation and esterification. Subsequently the 6-methyl alkyl nicotinate is converted to 6-methyl nicotinoyl acetic acid alkyl ester with an alkyl acetate in the presence of an alkali metal alcoholate. Finally the 6-methyl nicotinoyl acetic acid alkyl ester is hydrogenated with hydrogen to 3-hydroxy-3-(2-methyl-5-pyridyl)-propionic acid alkyl ester in the presence of a hydrogenation catalyst.

Also according to the invention, the new 3-hydroxy-3-(2-methyl-5-pyridyl)-propionic acid alkyl esters is acetylated with acetic anhydride to produce 2-methylpyridine-5-propionic acid alkyl ester. The respective acetylation intermediate product is either isolated or directly hydrogenolyzed in situ in the presence of a hydrogenation catalyst with hydrogen to the final product.

The oxidation of 5-ethyl-2-methylpyridine to 6-methyl alkyl nicotinate is the object of Swiss Pat. No. 654 577 and consequently is performed according to it. See also corresponding U.S. Pat. No. 4,579,953.

The subsequent conversion to 6-methyl nicotinoyl acetic acid alkyl ester occurs in the presence of an alkali metal alcoholate, advantageously in the presence of sodium alcoholate, corresponding to the ester radical of the corresponding alkyl acetate under conditions known in the art for Claisen condensations. The 6-methyl nicotinoyl acetic acid alkyl ester can be isolated and purified, but preferably is used as a raw product in the hydrogenation.

The hydrogenation preferably takes place in the presence of a usual hydrogenation catalyst. Preferably palladium on carbon is used in a concentration of 1 to 10 percent of Pd on carbon, most preferably 5 percent of Pd on carbon. Advantageously the hydrogenation is performed under a pressure of 1 to 15 bars, preferably at 5 to 10 bars.

The lower aliphatic carboxylic acids, preferably acetic acid or the aliphatic alcohols corresponding to the ester radical, such as, methanol, ethanol, propanol or butanol, are advantageously used as solvents. But operation can also occur in aprotic solvents, e.g., toluene.

Advantageously the hydrogenation is performed at a temperature in the range of 0° to 100° C., preferably at 50° to 80° C.

After the hydrogenation is completed, which lasts between 2 and 12 hours depending on the pressure, and after the usual work-up the 3-hydroxy-3-(2-methyl-5-pyridyl)-propionic acid alkyl esters can be isolated in good purity.

Advantageously the alkyl esters have 1 to 4 carbon atoms. 3-Hydroxy-3-(2-methyl-5-pyridyl)-propionic acid methyl ester and 3-hydroxy-3-(2-methyl-5-pyridyl)propionic acid ethyl ester are especially preferred alkyl esters.

The new compounds form intermediate products for use in the production of 2-methylpyridine-5-propionic acid alkyl esters. They either can be used directly as raw product from the preceding hydrogenation or can be especially purified for the following acetylation step.

The acetylation takes place with acetic anhydride, advantageously in the presence of a catalytic amount of a tertiary amine. Preferably 4-dimethyl-aminopyridine is used as the catalyst in an amount of 0.0001 mol to 0.01 mol in relation to 1 mol of 3-hydroxy-3-(2-methyl-5-pyridyl)-propionic acid alkyl ester. The added acetic anhydride itself can be used as a solvent, but usually, with regard to acetic anhydride, inert solvents such as methylene chloride, chloroform, carbon, tetrachloride, alkyl acetates such as ethyl acetate or even toluene are used.

The reaction temperature can vary over a range of 0° to 140° C., but advantageously the operation is conducted at a temperature between 50° and 80° C.

The resulting acetylation product can be isolated and purified but preferably it is further hydrogenolyzed in situ to the final product.

The hydrogenolysis takes place in the presence of a common hydrogenation catalyst, advantageously palladium, which is applied to a carbon support advantageously in a concentration of 1 to 10 percent, with hydrogen. The hydrogen pressure is advantageously chosen in a range of 1 to 15 bars, advantageously between 5 and 10 bars. The solvent usually corresponds to the solvent from the acetylation step, but advantageously it is additionally diluted with a lower organic carboxylic acid, e.g., acetic acid. The reaction temperature is advantageously between 0° and 100° C., most advantageously between 50° and 80° C.

After hydrogenolysis is completed, the final product can be isolated in the usual way, e.g., by subsequent neutralization and extraction. An optional purification can take place by means of high-vacuum distillation. According to the invention process, 2-methylpyridine-5-propionic acid alkyl esters with contents of greater than 97 percent and in yields of 50 to 60 percent, in relation to the 6-methyl alkyl nicotinate, are obtained. Preferably, 2-methylpyridine-5-propionic acid methyl ester and 2-methylpyridine-5-propionic acid ethyl ester are produced corresponding to the particularly advantageous intermediate products, respectfully, 3-hydroxy-3-(2-methyl-5-pyridyl)-propionic acid methyl ester and ethyl ester.

DETAILED DESCRIPTION OF THE INVENTION

As used herein, all parts, ratios, proportions and percentages are on a weight basis unless otherwise stated herein or obvious herefrom to one ordinarily skilled in the art.

EXAMPLE 1

Production of 2-methylpyridine-5-propionic acid ethyl ester

1.1 6-methyl nicotinoyl acetic acid ethyl ester 35.8 g (0.52 mol) of sodium methylate and 200 ml of toluene were put in a 750-ml sulfonation flask. The reaction mixture was heated to reflux temperature. A mixture of 55.7 g (0.33 mol) of 6-methyl nicotinic acid ethyl ester (produced according to Swiss Pat. No. 654 577) and 60.3 g (0.68 mol) of ethyl acetate was added drop by drop to the stirred suspension over 7 hour period. The suspension was stirred at reflux temperature for 22 hours and then cooled to 20° C. 200 ml of water and 25 ml of concentrated hydrochloric acid were added and the phases were separated. The water phase was extracted with toluene and the combined organic phases were evaporated. Then the evaporation residue was distilled under vacuum. 25.9 g of 6-methyl nicotinoyl acetic acid ethyl ester, having a boiling point of 112°–130° C./0.2–0.4 mbar and a content according to HPLC of 89.7 percent, was obtained (yield 33.6 percent, in relation to the 6-methyl nicotinic acid ethyl ester).

1.2 3-hydroxy-3-(2-methyl-5-pyridyl) propionic acid ethyl ester 10.0 g (0.048 mol) of 6-methyl nicotinoyl acetic acid ethyl ester (distilled) was dissolved in 200 ml of 95 percent ethanol, mixed with 1 g of 5 percent palladium on activated carbon and poured into a 1-liter autoclave. The autoclave was put under 10 bars of hydrogen and stirred at 20° C. The hydrogenation ended after 6 hours. The autoclave was opened, and the reaction solution filtered and evaporated. 10.0 g of 3-hydroxy-3-(2-methyl-5-pyridyl)-propionic acid ethyl ester remained, which according to NMR and DC was pure. The yield, in relation to the 6-methyl nicotinyl acetic acid ethyl ester, was 100 percent.

A sample was distilled (b.p. 130° C./0.2 mbar, yield of the distillation 94 percent, content according to GC 97 percent).

NMR (CDCl$_3$) δ1.25 (t, J=7 Hz, 3H ), 2.50 (s, 3H), 2.70 (m, 2H), 4.15 (q, J=7 hz, 2H), 4.50 (br, 1H), 5.15 (dd, J=11 and 5 Hz, 1H), 7.15 (d, J=10 Hz, 1H), 7.65 (dd, J=10 and 2 Hz, 1H), 8.35 (d, J=2 Hz, 1H).

IR (thin layer) cm$^{-1}$ 3200, 2980, 2920, 1730, 1600, 1565, 1490, 1440, 1370, 1280, 1250, 1200, 1160, 1035, 875, 835, 740.

MS 209 (M$^+$, 8%) 194 (5), 122 (100), 94 (23).

1.3 2-methylpyridine-5-propionic acid ethyl ester 45.9 g (0.22 mol) of 3-hydroxy-3-(2-methyl-5-pyridyl)-propionic acid ethyl ester was dissolved in 100 ml of ethyl acetate, and 50 ml (0.53 mol) of acetic anhydride and 0.1 g (0.82 mmol) of 4-dimethylaminopyridine were added. The solution was stirred for 6 hours at 20° C. and then evaporated. The residue was dissolved in 50 ml methylene chloride and 50 ml of 5 percent sodium hydroxide solution, the phases were separated and the organic phase was evaporated. 55.8 g of raw 3-acetoxy-3-(2-methyl-5-pyridyl)-propionic acid ethyl ester was obtained. This raw product was dissolved in 300 ml of acetic acid with 3.0 g of 5 percent palladium on carbon and fed into a 1-liter autoclave. The autoclave was put under 8 bars of hydrogen and stirred at 70° C. Hydrogenation was ended after 6 hours. The autoclave was cooled and opened, and the solution was filtered and evaporated. The residue was dissolved in 50 ml of water and brought to pH 8 by potassium carbonate. The solution was extracted three times with 100 ml of methylene chloride and the organic extracts were evaporated. 42.5 g of raw 2-methylpyridine-5-propionic acid ethyl ester was obtained. The raw product was distilled (b.p. 100°–110° C./1.0 mbar). 22.0 g of 2-methylpyridine-5-propionic acid ethyl ester was obtained, with a GC content of 92 percent. The yield, in relation to the 6-methyl nicotinoyl propionic acid ethyl ester, was 62.9 percent.

EXAMPLE 2

Production of 2-methylpyridine-5-methyl propionate

2.1 3-hydroxy-3-(2-methyl-5-pyridyl)-propionic acid methyl ester 61.1 g of raw 6-methyl nicotinoyl acetic acid methyl ester was produced from 51.3 g (0.33 mol) of 6-methyl nicotinic acid methyl ester (produced according to the method of Swiss Pat. No. 654 577), 45.9 g (0.82 mol) of sodium methylate and 49.6 g (0.67 mol) of methyl acetate according to the general method of Example 1.1. 60.4 g of this raw product was dissolved in 300 ml of acetic acid, 0.5 g of 5 percent palladium on activated carbon was added, and the solution was poured into a 1-liter autoclave. The hydrogenation was performed under a hydrogen pressure of 8 bars and at a temperature of 65° C., and it lasted 3.5 hours. The autoclave was cooled and opened, and the solution was filtered and evaporated. The residue was dissolved in 100 ml of water and 70 ml of methylene chloride, and adjusted to pH 7 with 52.8 g of 40 percent sodium hydroxide solution. The phases were separated, the water phase was extracted twice, each with 70 ml of methylene chloride, and the organic extracts were evaporated. 47.8 g of raw 3-hydroxy-3-(2-methyl-5-pyridyl)-propionic acid methyl ester was produced. 46.6 g of raw product was recrystallized from 45 ml of toluene. The dried pure product had a content, as indicated by GC, of 95.4 percent and a melting point of 74° to 76° C. The yield of 35.1 g corresponded to 53.7 percent, in relation to the 6-methyl nicotinic acid methyl ester used.

NMR (CDCl$_3$) δ2.50 (s, 3H), 2.70 (m, 2H), 3.70 (s, 3H), 4.00 (br, 1H), 5.15 (dd, J=11 and 6 Hz, 1H), 7.10 (d, J=9 Hz, 1H), 7.65 (dd, J=9 and 2 Hz, 1H), 8.40 (d, J=2 Hz, 1H).

IR (KBR) cm$^{-1}$ 3460, 3140, 3040, 2970, 2840, 1735, 1605, 1495, 1440, 1395, 1355, 1325, 1280, 1230, 1205, 1165, 1075, 1030, 980, 930, 910, 890, 860, 740.

MS 195 (M+, 10%) 180 (5), 122 (100), 94 (32).

2.2 2-methylpyridine-5-methyl propionate 80.0 g (0.35 mol) of recrystallized 3-hydroxy-3-(2-methyl-5-pyridyl)-propionic acid methyl ester was dissolved in 100 ml of toluene. 60.0 g (0.588 mol) of acetic anhydride and 0.1 g (0.0009 mol) of 4-dimethylaminopyridine were added, and the solution was stirred for 1 hour at 60° C. Then 20 ml of methanol was added. After 15 minutes, the solution was diluted with 250 ml of acetic acid, 1.5 g of 5 percent palladium on activated carbon was added, and the solution was poured into the autoclave. The hydrogenation was performed under 8 bars of hydrogen at 65° C. for 5.5 hours. At the end of the hydrogenation, the autoclave was cooled, and the solution was filtered and evaporated. The evaporation residue was dissolved in 100 ml of water and 100 ml of methylene chloride and adjusted to pH 7 with 87.9 g of 40 percent sodium hydroxide solution. The phases were separated, the aqueous phase was extracted with methylene chloride, and the combined organic extracts were evaporated. 71.5 g of raw 2-methylpyridine-5-propionic acid methyl ester was obtained. (Content according to GC, 91.5 percent; yield, 92.1 percent in relation to the 3-hydroxy-3-(2-methyl-5-pyridyl)-propionic acid methyl ester used.) The product was distilled to obtain a 97 percent product having with a boiling point of 100°-113° C./1-2 mbar. The yield of distilled product was 88.5 percent, in relation to the 3-hydroxy-3-(2-methyl-5-pyridyl)propionic acid methyl ester used.

EXAMPLE 3

2-methylpyridine-5-propionic acid methyl ester 48.0 g of raw 3-hydroxy-3-(2-methyl-5-pyridyl)propionic acid methyl ester was produced according to the method of Example 2.1 from 51.3 g (0.33 mol) of 6-methyl nictonic acid methyl ester. This raw product was not recrystallized but was dissolved with 35.8 g of acetic anhydride and 50 mg (0.41 mmol) of 4-dimethylaminopyridine in 50 ml of methylene chloride, and stirred at reflux temperature (40° C.) for 1.5 hours. 10 ml of methanol was added, and the solution was evaporated after 0.5 hours. The raw acetoxy compound was hydrogenated in 300 ml of acetic acid in the presence of 4 g of 5 percent palladium on activated carbon. The hydrogenation was conducted for 7 hours at a temperature of 50° C. and a hydrogen pressure of 5 bars. The 2-methylpyridine-5-propionic acid methyl ester was isolated from the reaction mixture by evaporation and extraction as in Example 2.2. 39.1 g of raw 2-methylpyridine-5-propionic acid methyl ester was produced with a content of 83.1 percent according to GC, which corresponded to a total yield of 56.0 percent in relation to the 6-methyl nicotonic acid methyl ester.

EXAMPLE 4

3-hydroxy-3-(2-methyl-5-pyridyl)-propionic acid methyl ester 49.7 g of raw 6-methyl nicotinoyl methyl acetate was produced from 51.3 g (0.33 mol) of 6-methyl nicotinic acid methyl ester, 37.3 g (0.67 mol) of sodium methylate and 49.6 g (0.67 mol) of methyl acetate according to the general method of Example 1.1. 49.1 g of this product was hydrogenated with 2.0 g of 5 percent palladium on activated carbon in 300 ml of toluene. The hydrogenation took 7 hours at a pressure of 8 bars of hydrogen and a temperature of 50° C. After hydrogenation, the solution was filtered and evaporated. The raw product was recrystallized from 40 ml of toluene. 21.0 g of 3-hydroxy-3-(2-methyl-5-pyridyl)propionic acid methyl ester was produced with a content of 95.5 percent (according to GC). The yield was 34.7 percent, in relation to the 6-methyl nicotinic acid methyl ester.

EXAMPLE 5

3-acetoxy-3-(2-methyl-5-pyridyl)-propionic acid methyl ester 10 g (0.05 mol) of 3-hydroxy-3-(2-methyl-5-pyridyl)-propionic acid methyl ester and 6.6 g (0.065 mol) of acetic anhydride were heated for 2 hours to reflux temperature (140° C.) without solvent. The solution was cooled, poured into 50 ml of water and adjusted to pH 8 with 8 mol of 25 percent ammonia solution. The product was isolated by extraction three times, each time with 50 ml of methylene chloride, and evaporation of the organic extracts. 11.2 g (92 percent) of the acetoxy compound was obtained.

EXAMPLE 6

3-Acetoxy-3-(2-methyl-5-pyridyl)-propionic acid ethyl ester 4.3 g (0.021 mol) of 3-hydroxy-3-(2-methyl-5-pyridyl)-propionic acid ethyl ester, 3.0 g (0.03 mol) of acetic anhydride, 2.7 g (0.034 mol) of pyridine and 0.17 g (0.0017 mol) of 4-dimethylaminopyridine were stirred at 0° C. for 24 hours. The solution was mixed with 25 ml of 5 percent sodium hydroxide solution and extracted twice, each time with 25 ml of methylene chloride. The organic extracts were evaporated; the residue (4.7 g) contained 3-acetoxy-3-(2-methyl-5-pyridyl)-propionic acid ethyl ester (yield 90.4 percent).

EXAMPLE 7

Comparison test or example

Hydrogenation of 6-methyl nicotinoyl ethyl acetate according to the method of Graef et al., J. Org. Chem., 11,257, (1946)

5 g (0.026 mol) of 6-methyl nicotinoyl ethyl acetate was dissolved in 40 ml of acetic acid and 0.3 g of 5 percent palladium on barium sulfate, and then three drops of 60 percent perchloric acid were added. The hydrogenation reaction was attempted under 1 bar of H$_2$ at 25° C., but no reaction was detected. 0.3 g of catalyst and three drops of perchloric acid were added, and the hydrogenation was continued at 80° C. under 1 bar of H$_2$. After 4 hours the solution was filtered and evaporated. The product was isolated by neutralization with aqueous potassium carbonate and extraction with chloroform. 5.3 g of raw product was obtained and purified by column chromatography. Only traces of 2-methylpyridine-5-propionic acid ethyl ester were obtained. The main product (63 percent yield) was 3-hydroxy-3-(2-methyl-5-pyridyl)-propionic acid ethyl ester.

What is claimed is:

1. Process for the production of a 3-hydroxy-3-(2-methyl-5-pyridyl)-propionic acid alkyl ester having the formula:

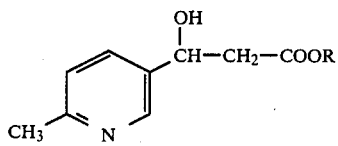

wherein R is a lower alkyl group, by converting 5-ethyl-2-methylpyridine, by the oxidation and esterification to a 6-methyl nicotinic acid alkyl ester, wherein the 6-methyl nicotinic acid alkyl ester in the presence of an alkali metal alcoholate with an alkyl acetate is converted to 6-methyl nicotinoyl acetic acid alkyl ester, and the 6-methyl nicotinoyl acetic acid alkyl ester is hydrogenated in the presence of a hydrogenation catalyst with hydrogen, said hydrogenation is performed at a pressure of 1 to 15 bars and the hydrogenation temperature is between 0° and 100° C.

2. Process as claimed in claim 1 wherein R is a methyl group.

3. Process as claimed in claim 1 wherein R is an ethyl group.

4. Process as claimed in claim 1, wherein the alkali metal alcoholate is a sodium ($C_1$–$C_4$) alcoholate.

5. Process as claimed in claim 4 wherein the alkyl acetate is an alkyl ($C_1$–$C_4$) acetate.

6. Process as claimed in claim 5, wherein palladium on carbon is used as the hydrogenation catalyst.

7. Process as claimed in claim 6 wherein the hydrogenation is performed at a pressure of 1 to 15 bars.

8. Process as claimed in claim 7 wherein the hydrogenation temperature is between 0° and 100° C.

9. Process as claimed in claim 1 wherein the alkylacetate is an alkyl ($C_1$–$C_4$) acetate.

10. Process as claimed in claim 1 wherein palladium on carbon is used as the hydrogenation catalyst.

11. Process as claimed in claim 1 wherein the hydrogenation is performed at a pressure of 1 to 15 bars.

12. Process as claimed in claim 1 wherein the hydrogenation is performed at a pressure of 1 to 15 bars and the hydrogenation temperature is between 0° and 100° C.

13. Process for the preparation of a 2-methylpyridine-5-propionic acid alkyl ester comprising acetylating a 3-hydroxy-3-(2-methyl-5-pyridyl)-propionic acid alkyl ester having the formula:

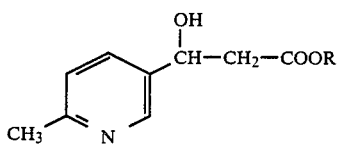

wherein R is a lower alkyl group, with acetic anhydride to provide an acetylation intermediate product, and hydrogenolyzing the actylation intermediate product with hydrogen in the presence of a hydrogenation catalyst to provide said 2-methylpyridine-5-propionic acid alkyl ester.

14. Process as claimed in claim 13 wherein said acetylation intermediate product is first isolated before it is hydrogenolyzed.

15. Process as claimed in claim 13 wherein said hydrogenolysis of said acetylation intermediate product is conducted in situ without isolation of said acetylation intermediate product.

16. Process as claimed in claim 13 wherein the acetylation is conducted in the presence of a tertiary amine as a catalyst.

17. Process as claimed in claim 13 wherein the acetylation is conducted in the presence of 4-dimethylaminopyridine as a catalyst.

18. Process as claimed in claim 13 wherein the acetylation is performed at a temperature of 0° to 140° C.

19. Process as claimed in claim 13 wherein palladium on carbon is used as the hydrogenation catalyst for the hydrogenolysis.

20. Process as claimed in claim 13 wherein the hydrogenolysis is performed under a pressure of 1 to 15 bars.

21. Process as claimed in claim 13 wherein the hydrogenolysis is performed at a temperature of 0° to 100° C.

* * * * *